United States Patent [19]

Moore

[11] Plant 4,484

[45] Nov. 13, 1979

[54] MINIATURE ROSE PLANT

[76] Inventor: Ralph S. Moore, 2519 E. Noble Ave., Visalia, Calif. 93277

[21] Appl. No.: 964,497

[22] Filed: Nov. 29, 1978

[51] Int. Cl.[2] ..... A01H 5/00

[52] U.S. Cl. ..... Plt./7

[58] Field of Search ..... Plt./7, 10

*Primary Examiner*—Robert E. Bagwill

[57] ABSTRACT

The subject of the present described invention is a new and distinct variety of miniature rose plant characterized by small quite double flowers of a distinct scarlet red color with buds of formal hybrid tea (exhibition) shape.

5 Drawing Figures

The present invention relates to a new and distinct variety of hardy, dwarf, busy type rose plant of the miniature class: the variety being primarily characterized—as to novelty—by scarlet red to orange red buds and flowers which in general color effect are similar to Fire Princess (miniature —U.S. Plant Pat. No. 3,084), The variety is further characterized by:

An abundance of bloom, with flowers borne singly or several to the stem in loose clusters.

Little or no fragrance.

A plant which is vigorous, or rounded bushy shape with semi-glossy, small foliage with pointed leaflets; the buds and flowers being similar in form and size to Kathy (miniature—U.S. Plant Pat. No. 3,246).

The plant, which has a normal height of 8–10 inches can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Little Chief, miniature (not patented) as the seed parent and Fire Princess (miniature—U.S. Plant Pat. No. 3,084) as the pollen parent.

Subsequent to origination of the variety I successfully asexually reproduced it, at Sequoia Nursery located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature. Variety name: Orange Pixie.

Flowers borne: Singly and several together (3 to 5 or more) on slender wirey stems.

Quantity of bloom: Abundant both outside and in greenhouse.

Bud:

*Peduncle.*—Quite long; slender but sturdy; erect; medium green, sometimes tinted bronze (outdoors); hairs — few or none.

*Before calyx breaks.*—Size — small. Form slender — ovoid: pointed with several foliaceous appendages and numerous very tiny hairs on surface of bud; with foliaceous parts extending beyond the tip of the bud equal to about one-half or less of its length. Color — medium green, occasionally tinted with bronze (outdoors).

*As calyx breaks.*—Color — medium to dark red near Carmine 21 overlaid with darker red on lower portion; in warm weather this color may be near Scarlet 19/1 to Geranium Lake 20/2 or 20/1. Opening: opens well in all weather.

Bloom:

*Size when fully open.*—Small, averaging about 30 mm or smaller.

*Petalage.*—Double — averaging about 60 petals, arranged regularly plus several small petaloids.

*Form.*—Flat at first, becoming more high centered, and later at maturity full with petals rolled loosely outward and downward. Open flower full, rounded, sometimes may show stamens.

Petals: Fairly thick; satiny on inside and on outside surface.

*Shape.*—Outside petals, broad lanceolate (nearly round) with rounded tip; intermediate — broad lanceolate with rounded tip; inside — lanceolate with short acute tip.

Color: Newly opened flower from a plant grown in plastic greenhouse (November 1978), Visalia, Calif.:

*Outside petal.*—Outside surface — neaer Cardinal Red 822/3 with both lighter and darker shading — small yellowish (near white) spot at base. Inside surface — near Geranium Lake 20 to Scarlet 19 overlaid with darker areas — small near white area at base.

*Intermediate petal.*—Outside surface — near Cardinal Red 822/3 with lighter shading and small near white spot at base. Inside surface — similar to outside petal.

*Inner petal.*—Outside surface — near Blood Red 820/20 with some darker areas and yellowish spot at base. Inside surface — same as intermediate petal.

*General color effect.*—Newly opened flowers — vibrant red with orange (fluorescent) sheen.

Note: In warmer weather the color is lighter, more toward Scarlet 19 or 19/1 with the orange (fluorescent) sheen. Three days open — color similar to newly opened flowers. Behavior — opens well in all weather. Color similar to Fire Princess but plant, foliage and flower are much smaller. Spent petals drop off. Flower longevity (June 1978) — plant in pot 6–8 days or longer. Cut flowers at living room temperature 5–7 days.

Reproductive Organs:

*Stamens.*—Several, sometimes none, arranged irregularly about pistils.

*Filaments.*—Very short, yellowish.

*Anthers.*—Well formed; yellow.

*Pollen.*—Little or none.

*Pistils.*—Average number.

*Styles.*—Fairly even; short length; bunched; color — greenish.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; small; leathery; semi-glossy.

*Leaflets.*—Shape: broad, nearly oval; apex acute; base rounded or rounded acute. Margin serrate. color: medium green; new growth — usually green; Rachis: medium strength; upper side may have a few tiny short prickles or hairs, grooved; underside sparsely thorny with few or no tiny prickles. Stipules: medium long; medium width; short to medium narrow points which turn out usually at about 45 degrees.

Growth:

*Habit.*—Dwarf; bushy; rounded; much branched.

*Growth.*—Free; vigorous; internodes short.

*Canes.*—Medium; slender; sturdy.

*Main stems.*—Color: medium green.

*Thorns.*—Average; slender; hooked slightly downward; color: brown. Prickles — none. Hairs: none.

*Branches.*—Color: medium green. Thorns: few; short length; slender; nearly straight; inclined slightly downward. Medium to short oval base. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded much branched habit, substantially as illustrated and described, characterized by buds and flowers which resemble the miniature rose Kathy (U.S. Plant Pat. No. 3,246) in size and shape and are of a color resembling the variety Fire Princess, miniature (U.S. Plant Pat. No. 3,084); and further characterized by a plant of dwarf compact habit which is easy to propagate from cuttings or by budding, with an abundance of flowers borne singly or several to the stem in loose clusters.

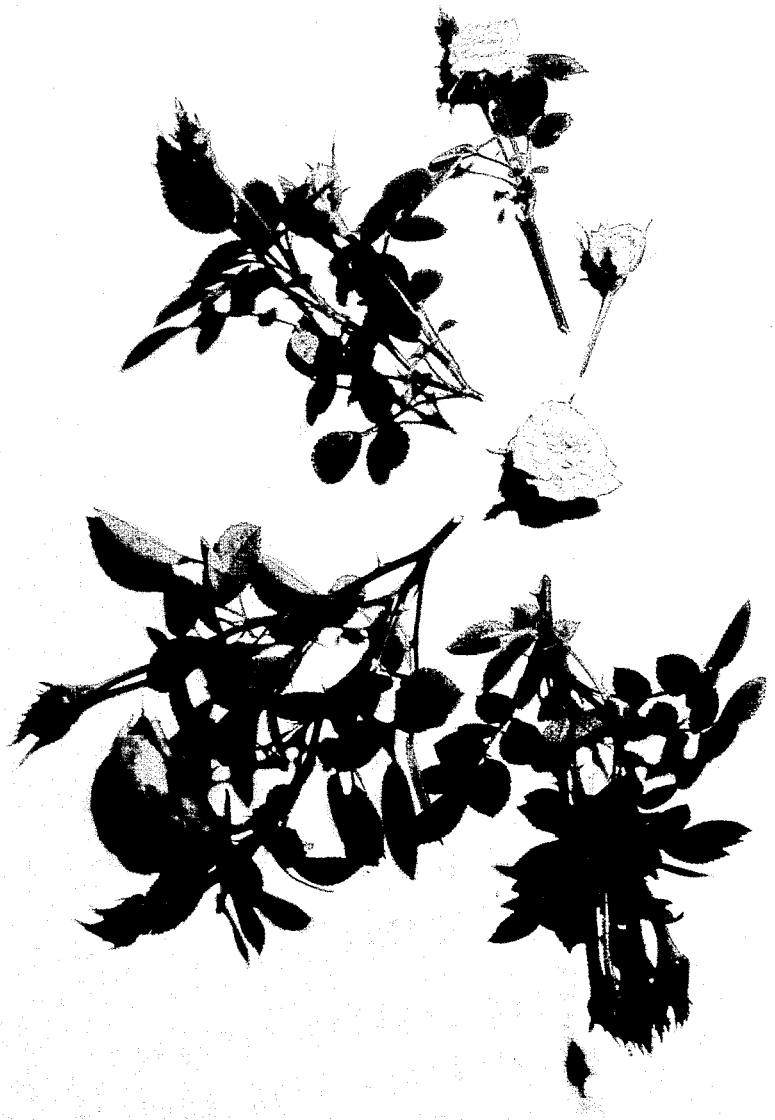

* * * * *